United States Patent [19]
Rothlein et al.

[11] Patent Number: 5,223,396
[45] Date of Patent: Jun. 29, 1993

[54] METHOD FOR DETECTING ORGAN TRANSPLANT REJECTION

[75] Inventors: Robert Rothlein; Steven D. Marlin, both of Danbury, Conn.

[73] Assignee: Boehringer Ingelheim Pharmaceuticals, Inc., Ridgefield, Conn.

[21] Appl. No.: 695,173

[22] Filed: May 3, 1991

[51] Int. Cl.$^5$ .............................................. C12Q 1/00
[52] U.S. Cl. .................................. 435/7.21; 436/501; 436/506; 436/509; 436/510; 436/518
[58] Field of Search ............... 436/501, 506, 509, 510, 436/518; 435/7.21

[56] References Cited
PUBLICATIONS

Marlin et al. Nature vol. 344 (Mar. 1990) pp. 70–72.

Dustin et al, The Journal of Immunology vol. 137, No. 1 (Jul. 1, 1986) pp. 245, 246 & 252–254.

*Primary Examiner*—Sam Rosen
*Attorney, Agent, or Firm*—Daniel Reitenbach; David E. Frankhouser; Mary-Ellen M. Timbers

[57] ABSTRACT

A method for the detection of the presence of inflammation in a patient by measuring the amount of circulating intercellular adhesion molecule (cICAM-1) in a sample of one or more bodily fluids of the patient and then comparing the amount of cICAM-1 in the sample to standards normal for the bodily fluid or fluids assayed. The amount of cICAM-1 can be measured using anti-ICAM-1 antibodies. Higher than normal amounts of cICAM-1 indicate the presence of inflammation. Also contemplated is a method for the detection of organ transplant or tissue graft rejection.

8 Claims, 6 Drawing Sheets

METHOD FOR DETECTING ORGAN TRANSPLANT REJECTION

FIELD OF THE INVENTION

This invention relates to a method for detecting inflammation in a patient by measuring the amount of circulating intercellular adhesion molecule-1 (cICAM-1) in bodily fluids of the patient. In particular, this invention relates a method for detecting inflammation in a patient by measuring the amount of cICAM-1 in bodily fluids of the patient using antibodies specific for intercellular adhesion molecule-1 (ICAM-1).

BACKGROUND OF THE INVENTION

Intercellular adhesion molecule-1 (ICAM-I) is a cytokine-inducible adhesion molecule expressed on cells of multiple lineages at sites of inflammation. See, e.g., Vejlsgaard et al, J. Amer. Acad. Demtol. 20: 782 (1989) and Sobel et al, Am. J. Pathol. 136: 1309 (1990). It is a ligand for at least 2 members of the CD18 family of leukocyte adhesion molecules (LFA-1 and Mac-1) and mediates, in part, granulocyte extravasation, lymphocyte mediated cytotoxicity and the development of specific immunological responses involving cell-cell interactions. See, e.g., Springer, T. A., Nature 346: 425 (1990). Antibodies to ICAM-1 have been shown to inhibit leukocyte adhesion to endothelial cells, granulocyte migration through endothelium, mitogen and antigen induced lymphocyte proliferation and mixed lymphocyte reactions in vitro. See, e.g., Smith et al, J. Clin. Invest. 82: 813 (1987). In vivo, antibodies to ICAM-1 inhibit neutrophil trafficking into inflamed lungs in rabbits, nonhuman primate kidney and heart allograft refection, and antigen induced airway eosinophil influx and airway hyperresponsiveness. See, e.g., Barton et al, J. Immunol. 143: 1278 (1989). Structurally, ICAM-1 is a member of the immunoglobulin supergene family with 5 immunoglobulin-like domains, a single transmembrane region and a short cytoplasmic tail. See, e.g., Staunton et al, Cell 52: 925 (1988). ICAM-1 has been identified as a receptor for the major rhinovirus group and a genetically engineered form of ICAM-1 lacking the cytoplasmic tail and transmembrane region has been shown to inhibit rhinovirus infection in vitro. Marlin et al, Nature 344: 70 (1990) (hereinafter referred to as "Marlin et al"), herein incorporated by reference.

It is the purpose of this invention to provide a method for the detection of inflammation in a patient by measuring the amount of a soluble form of ICAM-1 in circulation (cICAM-1) in the bodily fluids of the patient.

SUMMARY OF THE INVENTION

This invention relates to a method for detecting the presence of inflammation in a patient which comprises measuring the amount of cICAM-1 in a sample of one or more bodily fluids of the patient and then comparing the amount of cICAM-1 in the sample to standards normal for the bodily fluid or fluids assayed. Higher than normal amounts of cICAM-1 indicate the presence of inflammation.

DETAILED DESCRIPTION OF THE INVENTION

Figure 1:
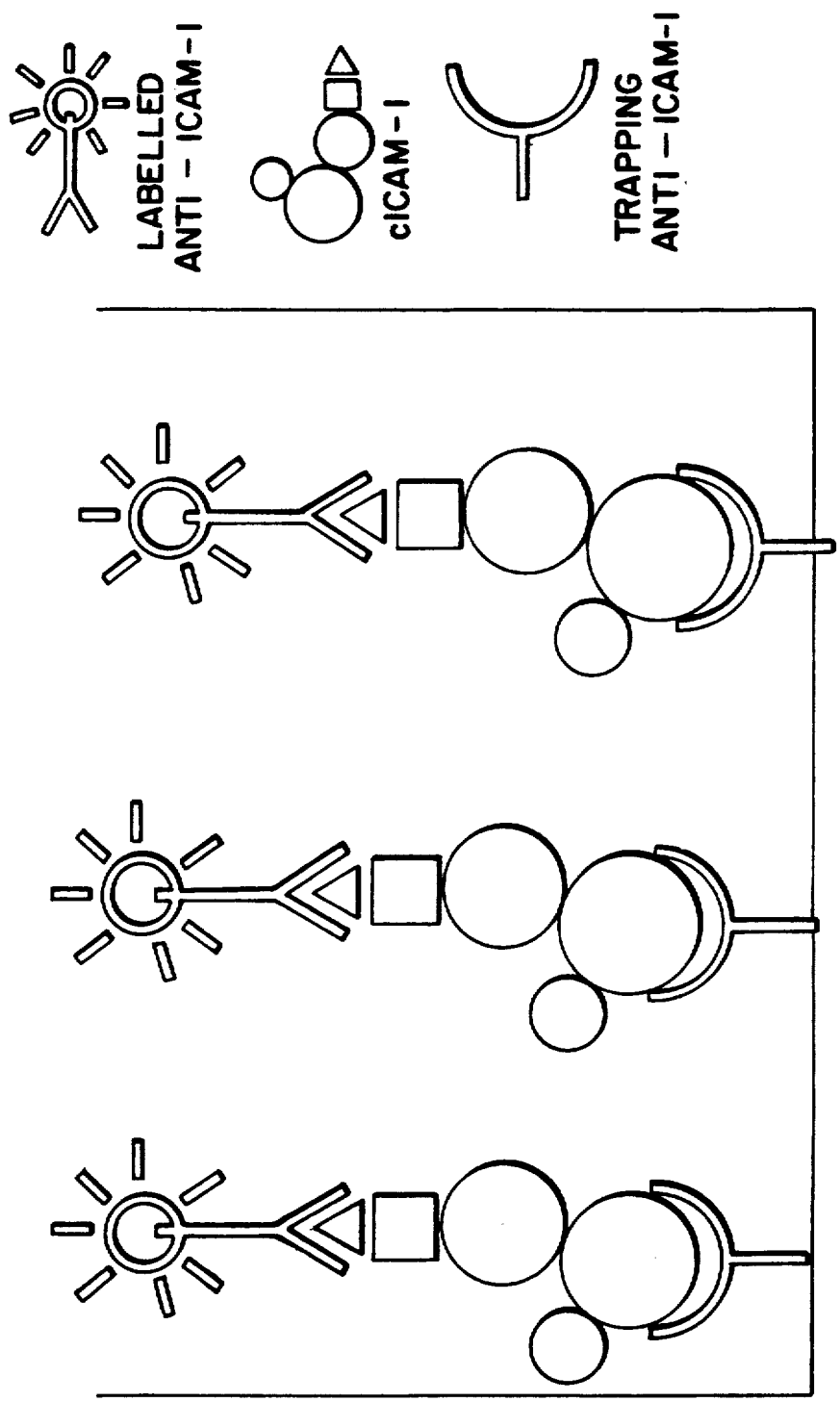
FIG. 1 is schematic representation of a sandwich assay for cICAM-1 using an immobilized anti-ICAM-1 antibody directed against domain 4 of ICAM-1 and a labelled anti-ICAM-1 antibody directed against domain 1 of ICAM-1.

The term "circulating ICAM-1" or "cICAM-1", for the purposes of this invention, means the soluble form of ICAM-1 in circulation in the bodily fluids of a patient including, for example, serum, bile, synovial fluid, and amniotic fluid. Most monoclonal antibodies that bind to ICAM-1 bind to cICAM-1. Additionally, immobilized cICAM-1 binds to LFA-1 bearing cells, demonstrating that cICAM-1 is structurally similar to genetically engineered sICAM-1 (Marlin et al). The apparent molecular weight of cICAM-1 is approximately 150 kD, as measured by size exclusion chromatography. sICAM-1, as prepared in Marlin et al, has a similar apparent molecular weight.

The discovery of cICAM-1 in bodily fluids and the observation that higher than normal levels of cICAM-1 in the bodily fluids of a patient are indicative of the presence of inflammation, is the basis for the assays useful in the method of this invention.

The term "inflammation", as used herein, is meant to include both the reactions of the specific defense system, and the reactions of the non-specific defense system.

As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases such as lupus erythematosus, rheumatoid arthritis, Reynaud's syndrome, multiple sclerosis etc., delayed type hypersensitivity response mediated by T-cells, etc. Chronic inflammatory diseases and the rejection of transplanted tissue and organs are further examples of inflammatory reactions of the specific defense system.

As used herein, a reaction of the "non-specific defense system" is intended to refer to a reaction mediated by leukocytes incapable of immunological memory.

Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukophoresis; ulcerative colitis; Crohn's disease; necrotizing enterocolitis; granulocyte transfusion associated syndromes; and cytokine-induced toxicity.

The selection of bodily fluids to be assayed will vary depending primarily on the type of inflammation to be detected. The bodily fluid or fluids selected should be either in contact with or produced at, the site of the inflammation. For the purposes of the method this invention, the bodily fluids should be substantially free of cells. For example, the presence of inflammation (and accordingly, elevated levels of cICAM-1) in synovial fluid may indicate the existence of rheumatoid arthritis. Kawasakis disease results in elevated levels of cICAM-1 in serum of patients afflicted with the disease. In monitoring the progress of liver transplants, elevated levels of cICAM-1 in the bile of a patient who received a liver transplant, indicate rejection of the transplant. Elevated levels of cICAM-1 in the amniotic fluid of a pregnant woman indicate a potential risk of a problem pregnancy.

Preferably, the assay useful in this invention is an immunoassay for detecting the presence of inflammation in a patient which comprises the steps of:

a) contacting a sample of one or more bodily fluids of the patient, with a first antibody capable of binding to ICAM-1 and a labelled second antibody capable of binding to ICAM-1;

b) determining the amount of bound labelled second antibody as a measure of the amount of cICAM-1 in the sample; and c) comparing the amount of cICAM-1 in the sample with standards of cICAM-1 normal for the bodily fluid or fluids assayed. Preferably, the antibodies are monoclonal antibodies.

Any immunoassay which produces quantifiable results can be used. This includes competitive and non-competitive binding assays, single site or multi-site. Preferably, the immunoassay used is a sandwich assay wherein the first antibody is immobilized and the labelled second antibody is soluble. Sandwich assays are described, for example, in U.S. Pat. Nos. 4,376,110 and 4,244,940.

In a more preferred embodiment of this invention, the immunoassay is a sandwich assay which comprises the steps of:

a) contacting a sample of one or more bodily fluids of a patient with an immobilized first antibody capable of binding to ICAM-1, the immobilized first antibody being insoluble in the sample, and with a soluble labelled second antibody capable of binding to ICAM-1, to form a final insoluble complex of the labelled second antibody, cICAM-1 and the immobilized first antibody;

b) determining the amount of labelled second antibody bound to the final insoluble complex, as a measure of the amount of cICAM-1 in the sample; and c) comparing the amount of cICAM-1 in the sample with standards of cICAM-1 normal for the bodily fluid or fluids assayed.

The immobilized first antibody is preferably immobilized on a solid support. The solid support can be any of the known support materials useful in prior art assays, such as cellulose, agarose, sepharose, polystyrene, nylon, polyacrylamide, latex, glass, magnetizable particles, nitrocellulose, etc. Preferably, the solid support is polystyrene. The antibody can be immobilized onto the solid support by any procedure which produces an immobilized antibody capable of binding to ICAM-1, such as by adsorption or covalent binding. Procedures for accomplishing such immobilization are well known to the art. For example, the antibody can be adsorbed in microtiter wells as described in Example 1 below and in Erlich et al, *Methods in Enzymology* 68: 443 (1979), or can be immobilized on a solid support using a bifunctional reagent as described in Kagedal et al, *Clinica Chimica Acta* 78: 103 (1977).

The amount of immobilized first antibody utilized in the method of this invention must be sufficient to bind a detectable quantity of cICAM-1. This amount will vary depending upon the type of inflammation to be detected, antibody, label used, etc., and should be determined empirically. In general, it is preferred that about 1 μg to about 10 μg of first antibody immobilized on the solid support per 50 μl of fluid sample, be utilized.

The labelled second antibody can be labeled by known means (e.g., with enzymatic, fluorogenic, radiometric, bioluminescent, affinity, chemiluminescent, colorimetric, etc., labels and markers), provided that the label does not have a deleterious effect on the binding of the antibody to cICAM-1. Procedures for accomplishing such labelling are well known to the art. For example, the procedure described in Example 1 can be used in biotinylating an antibody for the purposes of this invention, or a procedure such as the one described in Woodhead et al, *Clinical Chemistry* 29(8): 1474 (1983), can be used in labeling an antibody for the purposes of this invention. The amount of labelled second antibody utilized in the method of this invention must be sufficient to permit the detection of the cICAM-1 bound by the labelled second antibody. This amount will vary depending primarily upon the type of label used and should be determined empirically. Preferably, the second antibody carries a label that is capable of effecting a color change indicative of the presence of cICAM-1.

The final insoluble complex of labelled second antibody, cICAM-1, and immobilized first antibody bound to a solid support, can be produced using three assay procedures, referred to as a forward assay, a reverse assay, and a simultaneous assay. In the forward assay, the sample is first incubated with an immobilized first antibody for an appropriate period of time to form a first insoluble complex and then the first insoluble complex so formed is incubated with a soluble labelled second antibody for an appropriate period of time, to form the final insoluble complex. In the forward assay, the immobilized first antibody and the soluble labelled second antibody should be two different anti-ICAM-1 antibodies, which do not interfere with the binding of each other to the cICAM-1 molecule.

In the reverse assay, the sample is first incubated with a soluble labelled second antibody for an appropriate period of time to form a soluble complex of soluble labelled second antibody and cICAM-1. The soluble complex so formed is then incubated with an immobilized first antibody for an appropriate period of time to form the final insoluble complex. In the reverse assay, the immobilized first antibody and the soluble labelled second antibody should be two different anti-ICAM-1 antibodies which do not interfere with the binding of each other to the cICAM-1 molecule.

In the simultaneous assay, the sample is incubated with an immobilized first antibody and a soluble labelled second antibody at the same time to form the final insoluble complex. In the simultaneous assay, the immobilized first antibody and the soluble labelled second antibody should be two different anti-ICAM-1 antibodies, which do not interfere with the binding of each other to the cICAM-1 molecule.

The incubation conditions for each of the steps of the forward, reverse and simultaneous assays can vary, depending on time, temperature, and final incubation volume, but, preferably, each incubation step should be conducted for at least 15 minutes, more preferably for 30 minutes or longer, at room temperature or higher, more preferably, at 37° C.

After the incubation, the final insoluble complex is separated from the incubation medium (i.e., sample, unbound soluble labelled second antibody, etc.). Since the final insoluble complex is insoluble in the incubation medium, it can be separated from the incubation medium by conventional means.

The uptake of the soluble labelled second antibody is directly related to the presence of the cICAM-1 bound to the complex. The amount of label associated with the final insoluble complex can be determined by at least two methods: (1) direct quantitation of the label associated with the final insoluble complex, or (2) indirect quantitation of the label remaining in the incubation medium after separation and then subtracting the amount from the total label offered. The appropriate quantitation procedure will depend largely on the label used.

The anti-ICAM-1 antibodies useful in the method of this invention can be polyclonal, monoclonal or recombinantly produced. Techniques useful in the preparation of the anti-ICAM-1 antibodies are well known in the art. See, e.g., Kohler and Milstein, Nature 356: 495 (1975); U.S. Pat. No. 4,816,567; Rothlein et al, supra, and European Patent Application Serial No.289,949.

Other ligands of ICAM-1, such as LFA-1, may also be used to detect and measure cICAM-1 in the bodily fluids of a patient.

The following examples illustrate the method of this invention.

EXAMPLE 1

Detection of cICAM-1 in Human Sera

Sera from 10 normal individuals were compared to sera from 4 patients suffering from leukocyte adhesion deficiency (LAD) and to sera from 12 patients suffering from Kawasakis disease, to determine if there were detectable amounts of cICAM-1 in serum samples.

A. Preparation of Biologicals

Soluble ICAM-1 (sICAM-1) was prepared as described in Marlin et al; serially diluted in 1% bovine serum (Sigma, St. Louis, Mo.) Dulbecco's phosphate-buffered saline (Media Tech, Washington, D.C.) (BSA-dPBS); and aliquots frozen at −70° C.

Sera from normal human blood was collected into sterile Vacuutainers from drug free donors (10) by venipuncture. Blood was allowed to clot for at least one-half hour prior to collection of sera. Sera from leukocyte adhesion deficiency (LAD) patients (4) were obtained from Dr. Donald Anderson of Baylor University, Houston, Tex. Sera from patients with Kawasakis disease (12) were obtained from Dr. Jane Neuberger and Dr. Fred Rosen of the Center for Blood Research, Inc., Boston, Mass.

B. Preparation of Monoclonal Antibodies

Antibodies RR1/1 and R6.5 directed against domains 1 and 2 of ICAM-1 were prepared as described in Rothlein et al, J. Immunol. 137: 1270 (1986) and European Patent Application Serial No. 289,949, respectively.

Antibody CL203.4, directed against domain 4 of ICAM-1, was provided by Dr. Soldano Ferrone of New York Medical College, Valhalla, N.Y.

Antibody CA7, directed against domain 5 of ICAM-1, was prepared as follows:

BALB/C mice were subcutaneously immunized with 150 μg of sICAM-1 in 0.2 ml of complete Freunds adjuvant:saline (1:1 emulsion) on day −76; 100 μg of sICAM-1 in incomplete Freund's adjuvant:saline (1:1 emulsion) in 0.2 ml on day −45. On days −4 and −3, the mice were further immunized with 150 μg of sICAM-1 intraperitoneally. A fusion was then performed on day 0 between the spleens of the immunized mice and P3x63Ag8.658 myeloma cells using the protocol described in Rothlein et al, J. Immunol. 139: 1270 (1986). The resultant hybridoma antibodies were screened by ELISA for their ability to bind to sICAM-1 on plates. Selected hybridomas were subcloned twice. CA7 was determined to bind to domain 5 of ICAM-1 by immunoperoxidase staining of cytocentrifuge preparations of COS cells transfected with various constructs of ICAM-1 deletion mutants obtained from Dr. Donald Staunton and Dr. Timothy Springer, Center for Blood Research, Inc., Boston, Mass.

Anti-LFA-1 (anti-CD11a) antibody R3.1 was prepared as described in Smith et al, J. Clin. Invest. 82: 1746 (1988).

Antibodies were biotinylated as described in Guesdon et al, J. Histochem. Cytochem. 27: 1113 (1979).

C. ELISA for cICAM-1

CL203.4 (10 μg/ml in DPBS) was added to each well in 96 well flat bottom E.I.A. microtiter plates (Linbro) at 50 μl/well at room temperature for 1 hour. Wells were then washed three times with DPBS and then blocked with 200 μl of 2% BSA-DPBS for 1 hour at 37° C. Wells were then flicked empty and a titration of sICAM-1 standards (8 to 1024 ng/ml) and sera samples (titrated in 1% BSA-DPBS) were then added (50 μl/well) in triplicate for 1 hour at 37° C. Wells were then washed three times with DPBS. Biotinylated R6.5 was then added to each well, at 2 μg/ml (50 μl/well) for 30 minutes at 37° C. Wells were then washed three times with DPBS. 50 μl/well of horseradish peroxidase streptavidin (Zymed, San Francisco, Calif.) (1:4000) was then added to each well for 30 minutes at 37° C., followed by three washes with DPBS and one wash with substrate buffer (Zymed). 50 μl/well of 2,2 azino-di(3-ethylbenzthiazoline)-sulfonic acid (ABTS) (Zymed) in substrate buffer was then added. The plates were then read on a Dynatech Microtiter ELISA reader (410 nm) until maximum OD readings were obtained. Mean OD readings were calculated and cICAM-1 concentrations were calculated from the regression curve generated from the sICAM-1 titration.

The results from this ELISA for the sera from normal patients and for sera from LAD patients, are presented in Table 1 below

TABLE 1

| cICAM-1 in Sera | |
|---|---|
| NORMAL HUMAN SERA (ng/ml) | LAD SERA (ng/ml) |
| 189 | 335 |
| 223 | 687 |
| 110 | 372 |
| 141 | 363 |
| 251 | |
| 81 | |
| 109 | |
| 104 | |
| 122 | |
| 233 | |
| MEAN: 156 | MEAN: 439 |

Figure 2:
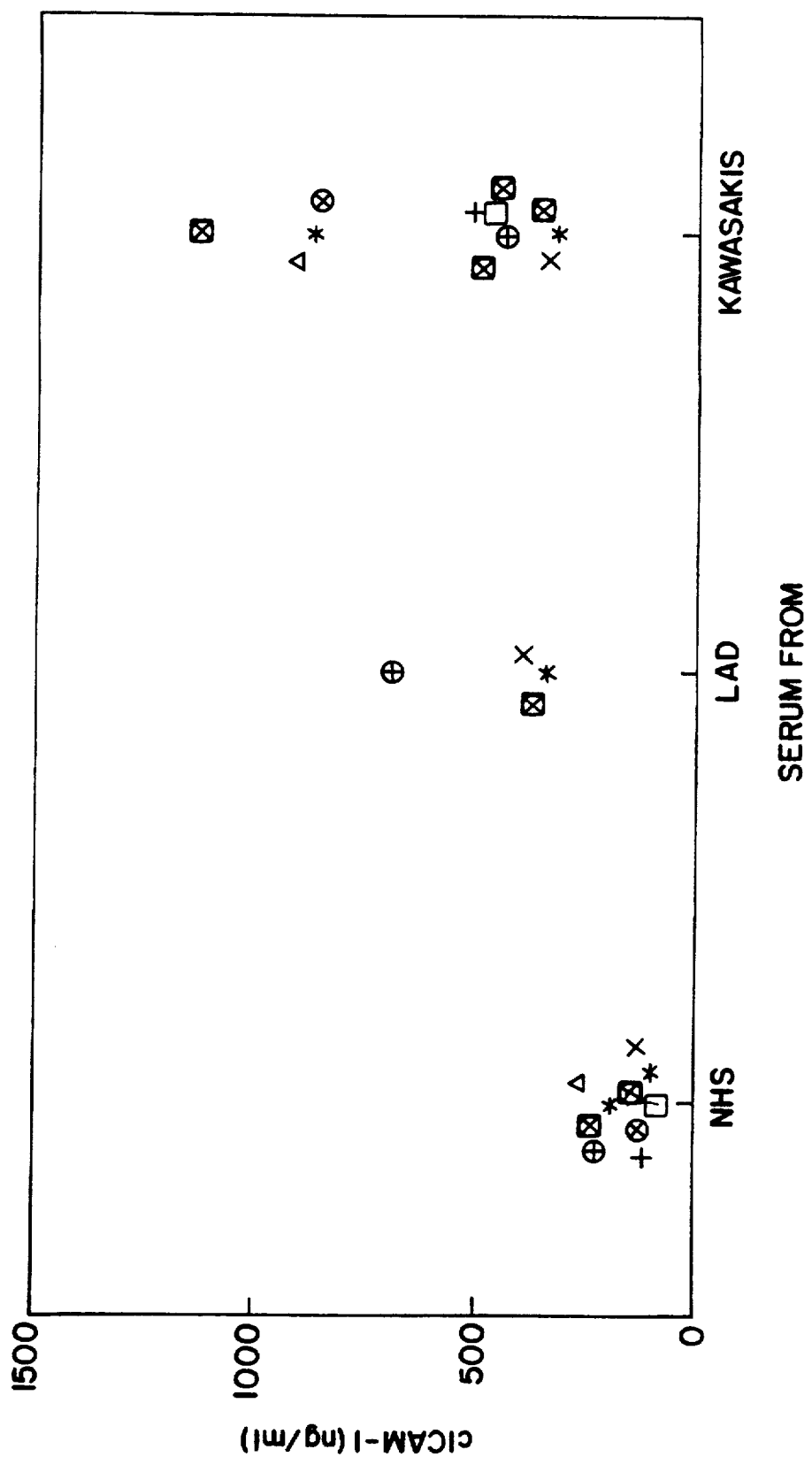
FIG. 2 is a graphic representation of cICAM-1 levels in sera from patients with normal serum, LAD patients and patients with Kawasakis disease.

FIG. 2 is a graphic depiction of the cICAM-1 levels found using this ELISA in sera from normal patients (NHS), from LAD patients, and from Kawasakis patients.

These results indicate that cICAM-1 is present in serum and that it retains the functional epitope recognized by CL203.4 on domain 4 and the functional epitope recognized by R6.5 on domain 2.

D. Cell Adhesion Assay

50 μl of CA7 (10 μg/ml) was added to each well of 96 well flat bottom E.I.A. microtiter plates (Linbro) at room temperature for 1 hour. Wells were then washed three times with DPBS and blocked with 200 μl of 2% BSA-DPBS for 1 hour at 37° C. 100 μl of normal human sera or 100 ng of sICAM-1 in 1% BSA-DPBS were then added to each well and incubated for 1 hour at 37° C. Wells were then washed three times with DPBS. 50 μl of RPMI-1640 (Gibco, Grand Island, N.Y.) supplemented with 50 μg/ml of gentamycin, 1 mM L-glutamine and 10% heat inactivated fetal bovine serum (Gibco) (complete medium), R3.1(100 μg/ml), R6.5 (100 μg/ml), or CL203.4 (100 μg/ml) were then added to the appropriate wells. SKW-3 cells (human T-lymphocyte cells from Sloan-Kettering Wallace, Sloan-Kettering Memorial, Rye, N.Y.) (50 μl of $2 \times 10^6$ cells/ml) in complete medium, were then added to each well and incubated for 30 minutes at 37° C. The nonadherent cells were gently washed off with RPMI-1640. The number of adherent cells was determined by mitochondrial reduction of MTT (3[4,5-dimethylthiazol-2-yl]-22,5 diphenyl-tetrazolium bromide:thiazole blue) (Sigma) as follows: The adherent cells were incubated with 100 μl of complete medium and 20 μl of MTT (5 mg/ml) for 3 hours at 37° C. The reduced MTT crystals so produced were solubilized with 60 μl/well of 1% Triton-X100 (Biorad, Richmond, Calif.) in 0.1N HCl. Plates were microwaved to gently heat the MTT precipitate. 10 μl of ethanol was added to remove any detergent bubbles. OD of the wells was then determined at 570 nM on a Dynatech Microtiter ELISA reader.

The above-described assay was repeated using the same procedure except that: (1) no sICAM-1 and no human serum was added to the wells; (2) the wells were initially incubated with R6.5 instead of CA7; or (3) the wells were initially incubated with BSA instead of CA7.

The results of this assay are listed in Table 2 below.

TABLE 2

| | | SKW-3 Adhesion | | | |
|---|---|---|---|---|---|
| Trap | Block | sICAM-1 MTT OD | sICAM-1 % Inhib. | Serum MTT OD | Serum % Inhib. |
| CA7[1] | Media | 427 | — | 458 | — |
| CA7 | R3.1 | 40 | 91 | 16 | 97 |
| CA7 | R6.5 | 95 | 75 | 137 | 70 |
| CA7 | CL203.4 | 417 | 3 | 503 | 0 |
| R6.5 | — | 0 | — | 0 | — |
| BSA | — | 0 | — | 0 | — |

[1]Using CA7 as the trapping antibody in the absence of sICAM-1 and human serum resulted in no SKW3 cell adherence.

The results in Table 2 above demonstrate that cICAM-1 in human serum retains its capacity to mediate LFA-1 dependent adhesion. Binding of SKW-3 cells were inhibited by both the anti-LFA-1 antibody (R3.1) and the anti-ICAM-1 antibody which binds to domains 1 and 2 of ICAM-1 (R6.5). These results indicate that cICAM-1 retains functional epitopes of domains 1, 2 and 5.

EXAMPLE 2

Detection of Pathological Pregnancy

A. Preparation of Biological Materials sICAM-1 was prepared as described in Example 1A.

Amniotic fluid samples were obtained from the following clinical groups: (1) samples obtained by amniocentesis for genetic evaluation in association with advanced maternal age, at 16 weeks gestation (39); (2) samples obtained by amniocentesis for genetic evaluation following an elevated concentration of alpha-fetoprotein in the amniotic fluid (21); (3) samples obtained by amniocentesis for pulmonary maturity or at cesarean section with delivery prior to 37 weeks gestation (12); (4) samples obtained at cesarean section or by transcervical catherization at the time of placement of fetal monitoring electrode, with delivery at term (10).

Maternal serum alpha-fetoprotein concentrations were determined by radioimmunoassay. Elevated values were defined as >2.0 multiples of the medium for gestational age and used corrections for maternal weight and race. In all cases in which maternal serum alpha-fetoprotein concentrations were elevated, amniotic fluid alpha-fetoprotein concentrations were normal.

B. Preparation of Monoclonal Antibodies

Monoclonal antibodies were prepared as described in Example 1B.

C. ELISA

The same assay as described in Example 1C was used except that the amniotic fluid samples were substituted for the sera samples.

The results of this ELISA are listed in Table 3 below.

TABLE 3

| cICAM-1 Levels in Amniotic Fluid | | |
|---|---|---|
| Gestational Age | Total Samples | cICAM-1 Level (ng/ml) ± SD |
| 16 Weeks Normal MSAFP[1] | 39 | 33 ± 8 |
| 16 Weeks Elevated MSAFP[1] | 21 | 131 ± 31 |
| Term Spontaneous Del. | 5 | 192.5 |
| Term Cesaraen | 4 | 140 ± 35 |

[1]Maternal serum alpha-fetoprotein

TABLE 4
cICAM-1 Levels in Preterm Deliveries

| Condition | Total Samples | cICAM-1 Level (ng/ml) ± SD |
|---|---|---|
| Spontaneous Del. | 5 | 718 |
| Other Delivery[1] | 4 | 265 |
| Non-Inflamed[2] | 10 | 336 ± 69 |
| Inflamed[2] | 2 | 1034 |

[1] Cesaraen
[2] Uterine compartment

Figure 3:
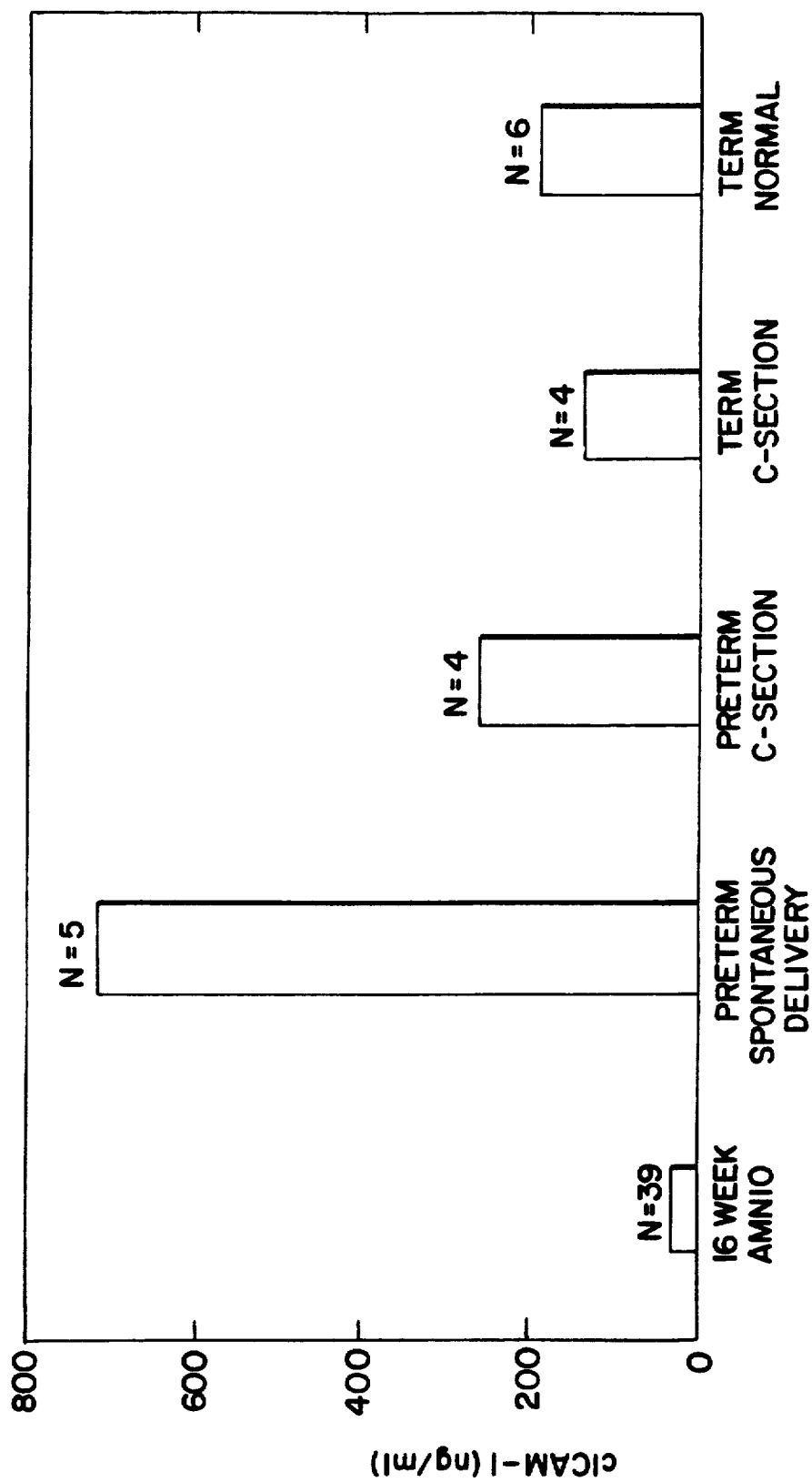
FIG. 3 is a graphic representation of cICAM-1 levels in the amniotic fluid of pregnant women at 16 weeks gestation, pregnant women who had a preterm spontaneous delivery, pregnant women who had preterm delivery by c-section, pregnant women who had a delivery at term by c-section and pregnant women who had a normal delivery at term.

FIG. 3 is a graphic depiction of the average (mean) levels of cICAM-1 in the amniotic fluid present at different gestational ages and conditions, determined using the ELISA described above.

These data show that a higher than normal level of cICAM-1 in the amniotic fluid prior to delivery at term, indicates a risk of an abnormal pregnancy.

EXAMPLE 3

Detection of cICAM-1 in Synovial Fluid of Arthritic Patients

A. Preparation of Biological Materials sICAM-1 was prepared as described in Example 1A.

Samples of synovial fluid from patients suffering from rheumatoid arthritis (8), osteoarthritis (4), psoriatic arthritis (1), gouty arthritis (1) and chondrocalcinosis (1) were collected by arthroscopy.

B. Preparation of Monoclonal Antibodies

Monoclonal antibodies were prepared as described in Example 1B.

C. ELISA cICAM-1 levels were measured using the ELISA described in Example 1C, substituting the samples of synovial fluid for the sera samples.

Figure 4:
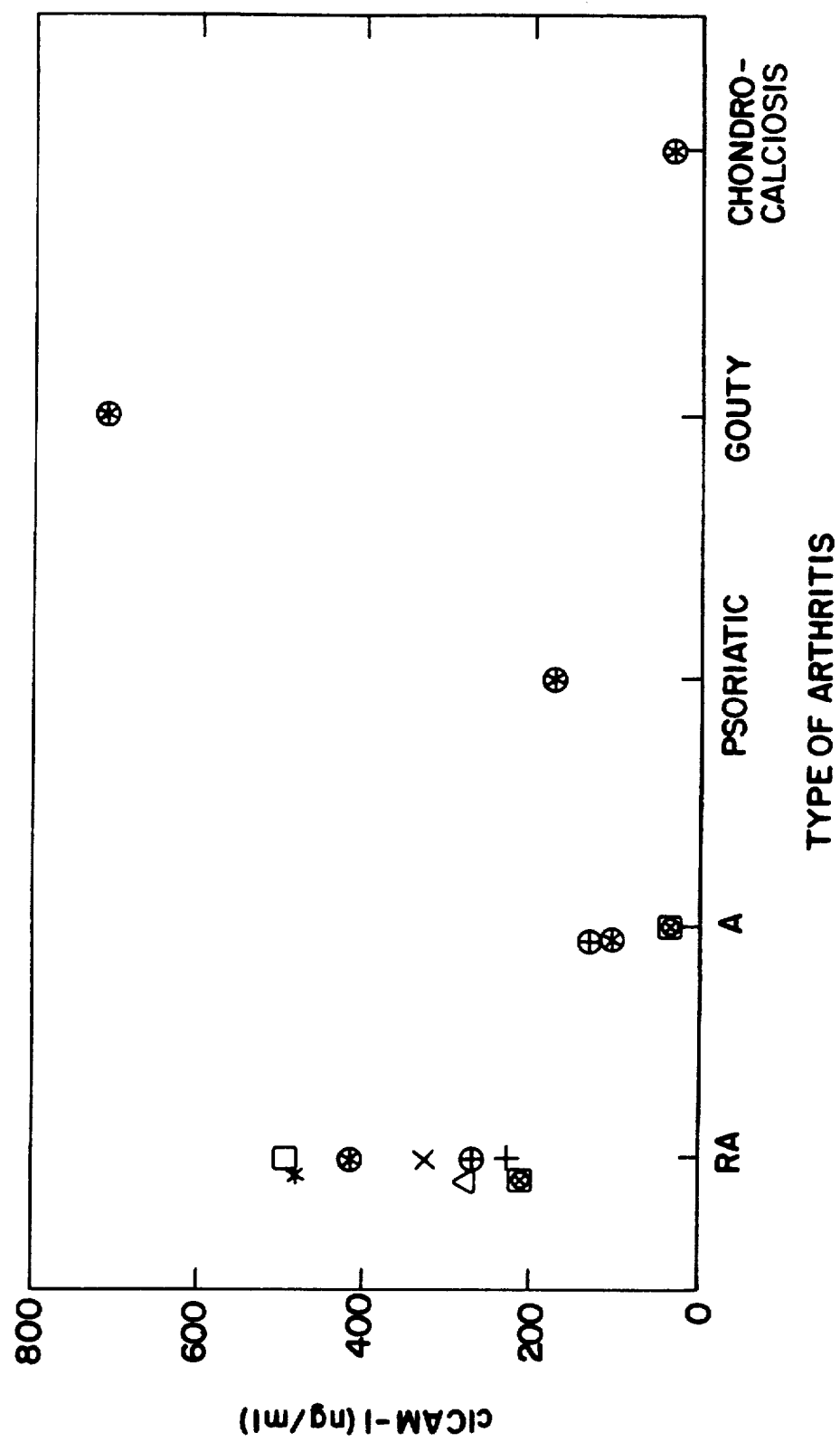
FIG. 4 is a graphic representation of cICAM-1 levels in synovial fluid of patients with rheumatoid arthritis (RA), osteoarthritis (OA), psoriatic arthritis, gouty arthritis, and chondrocalciosis.

The results of this assay are graphically depicted in FIG. 4. Samples from patients suffering from rheumatoid arthritis, which is accompanied by inflammation, contained elevated levels of cICAM-1 whereas patients suffering from osteoarthritis, which is not accompanied by inflammation, did not contain elevated levels of cICAM-1.

EXAMPLE 4

Detection of cICAM-1 in Bile of Liver Transplant Patients

A. Preparation of Biological Materials sICAM-1 was prepared as described in Example 1A.

Samples of bile and plasma from liver transplant patients who rejected the transplant (14), who had complications after the transplant (7) and who were stable after the transplant (10), were collected each day for 2-15 days after transplantation of the liver, as described in Adams et al, The Lancet, Mar. 4, 1989, pp. 469-471.

B. Preparation of Monoclonal Antibodies

Monoclonal antibodies were prepared as described in Example 1B.

C. ELISA cICAM-1 levels in the bile samples were measured using the ELISA described in Example 1C, substituting the bile samples for the sera samples.

Figure 5A:
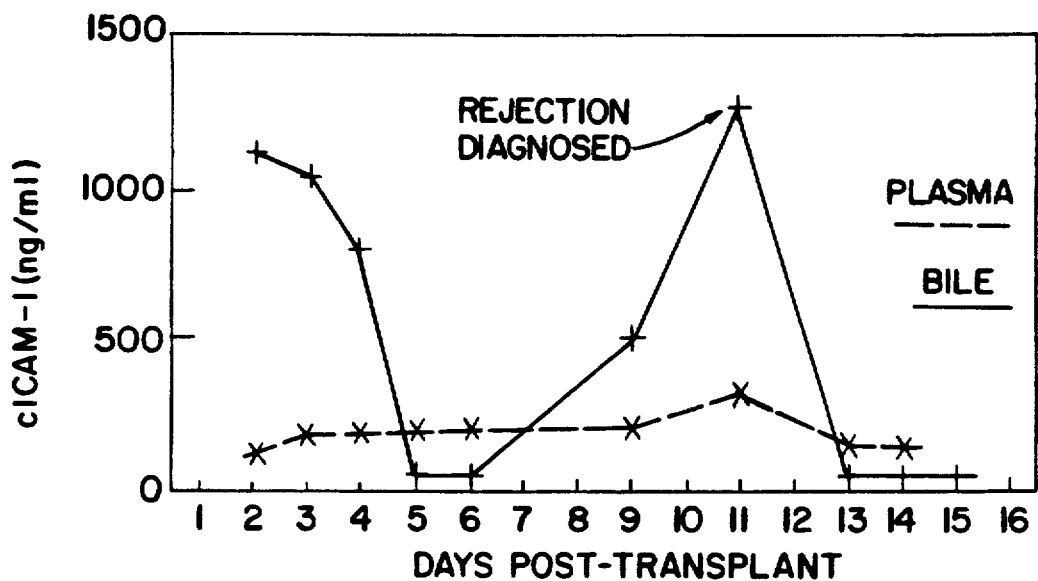
FIG. 5 is a graphic representation of cICAM-1 levels in the bile and plasma of a patient rejecting a liver transplant and a non-rejecting patient, over a period of time from 2 days post-transplant to 15 days post-transplant.
Figure 5B:
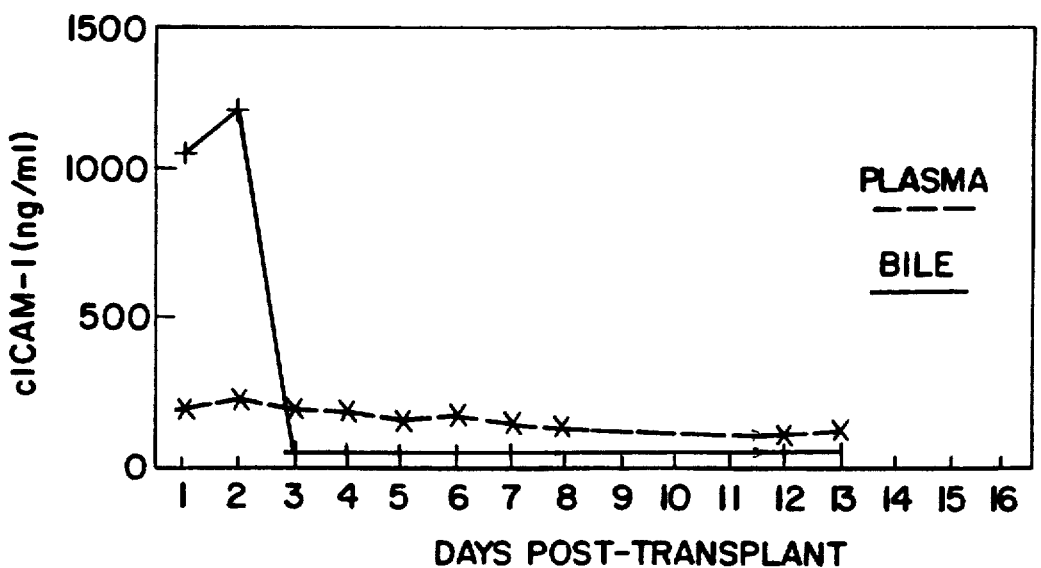

FIG. 5 depicts the levels of cICAM-1 in the samples of bile and plasma of a patient rejecting the transplant and in the samples of bile and plasma of a non-rejecting patient, over the course of 15 days post-transplant. Additional immunosuppressive therapy was instituted after 11 days and resulted in a drop of cICAM-1 levels in the rejecting patient.

Figure 6:
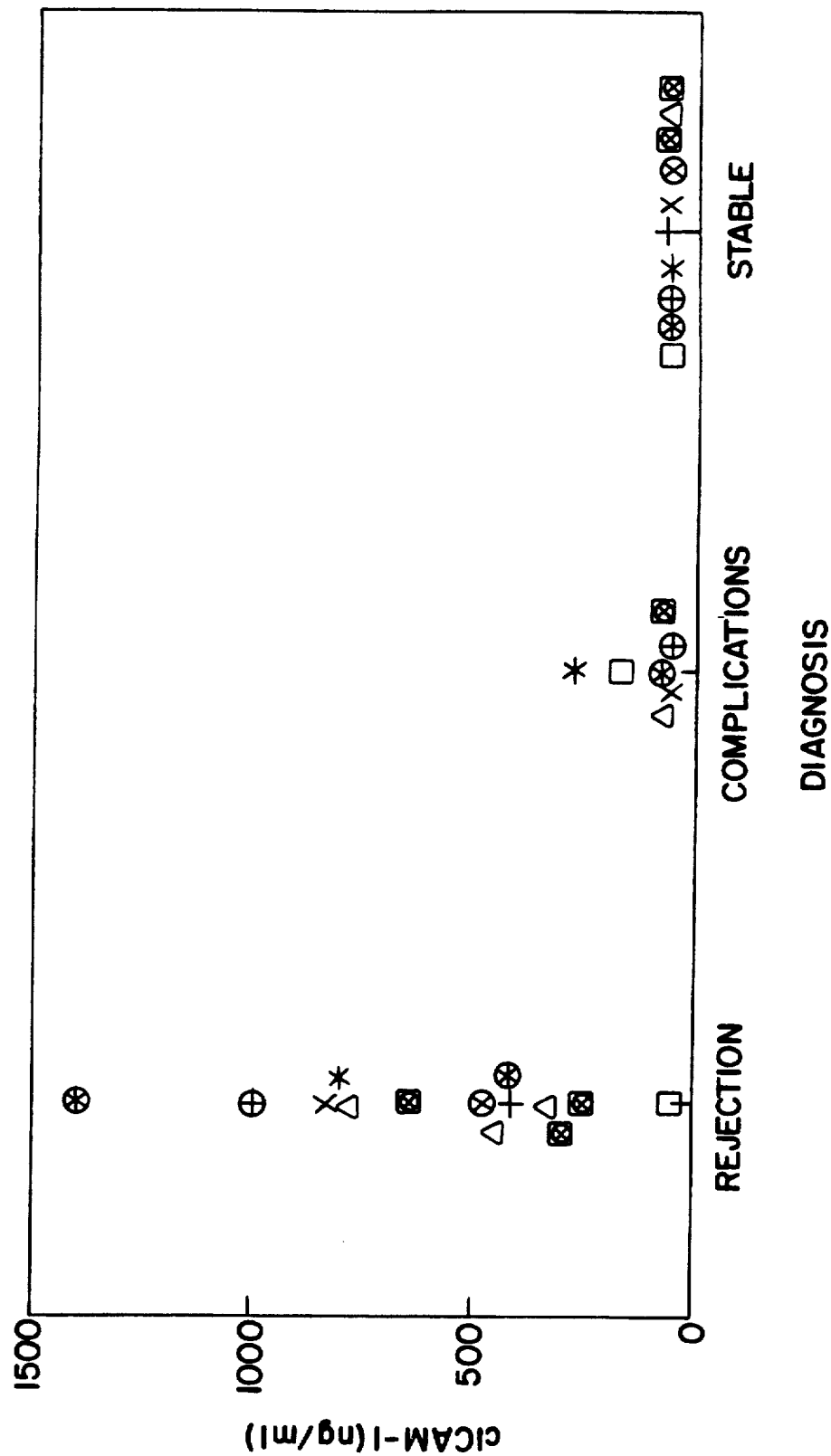
FIG. 6 is a graphic representation of cICAM-1 levels in the bile of liver transplant patients who rejected the transplant, who had complications, and who were stable.

FIG. 6 depicts the level of cICAM-1 measured in the samples of patients who rejected the transplanted liver at the time of diagnosis of rejection, the level of cICAM-1 measured in the samples of patients who experienced complications with the transplant, and the level of cICAM-1 in the samples of stable patients. With the exemption of one sample, all of the samples of the patients who rejected the transplanted liver contained elevated levels of cICAM-1. The samples from the stable (non-rejecting) patients contained normal levels of cICAM-1.

EXAMPLE 5

Detection of cICAM-1 in Serum of Patients with Human Malignant Melanoma

A. Preparation of Biological Materials sICAM-1 was prepared as described in Example 1A.

Sera were obtained from patients with confirmed Stage I (14), Stage II (24) and Stage III (18) cutaneous malignant melanoma, and from 12 normal individuals. Stage I disease was defined as the presence of a primary lesion with no clinically observable metastatic disease at the time of serum collection; Stage II disease was defined as metastasis to regional lymph nodes, local recurrence with or without regional lymph node involvement, or initial presentation of melanoma in a single lymph node group with no identifiable primary lesion; and Stage III disease was remote cutanious, subcutaneous, or visceral metastases. Survival was measured in months and was defined as the time from diagnosis to date of evaluation or death.

B. Preparation of Monoclonal Antibodies

Monoclonal antibodies were prepared as described in Example 1B.

C. ELISA cICAM-1 levels in the sera samples were measured using the ELISA described in Example 1C.

The results of this assay are listed below in Table 5.

TABLE 5
cICAM-1 in Serum of Patients with Malignant Melanoma

| Patients (No.) | cICAM-1 (Mean ± SEM[1]) | Range | % Positive Sera[2] |
|---|---|---|---|
| Control (12) | 166.0 ± 17.5 | 81–251 | 0 (0/12) |
| Stage I (14) | 406.2 ± 33.4[3] | 265–661 | 93 (13/14) |
| Stage II (24) | 232.9 ± 18.7 | 97–456 | 25 (6/24) |
| Stage III (18) | 303.8 ± 30.4[4] | 78–493 | 60 (11/18) |

[1] ng/ml of plasma (SEM = Standard Error of the Mean)
[2] Positive serum = >288.0 ng/ml
[3] p < .001 when compared with control or Stage II patients
[4] p < .01 when compared with control

TABLE 6
Survival in Stage II and Stage III Melanoma Patients with Elevated Levels of cICAM-1

| Patients (No.) | cICAM-1[1] | Survival[2] (+SEM) | Range |
|---|---|---|---|
| Stage II (6) | elevated | 25.8 ± 5.4 | 7–41 |
| Stage II (18) | normal | 38.8 ± 2.2[3] | 11–50 |
| Stage III (7) | elevated | 33.6 ± 6.3 | 18–66 |
| Stage III (6) | normal | 64.3 ± 13.1[4] | 35–120 |

[1] Level of serum cICAM-1 in "elevated" positive patients >288.0 ng/ml; "normal" patients <288.0 ng/ml
[2] In months
[3] p < .01 when compared with Stage II "elevated patients"
[4] p < .05 when compared with Stage III "elevated patients"

Serum levels of cICAM-1 were significantly elevated in patients with Stage I and III melanoma, and markedly enhanced in Stage II patients. Abnormally high serum levels of cICAM-1 were present in 93% of Stage I, 25% of Stage II, and 60% of Stage III patients, but were not observed in normal individuals.

Stage I patients, presumably with the least tumor burden, had both significantly ($p < 0.001$) increased levels of cICAM-1 and an extremely high incidence (93%) of elevated levels of cICAM-1. All melanoma patients had unusually high levels of serum cICAM-1. In Stage II melanoma patients with elevated levels of cICAM-1, a significant reduction in mean survival was observed when compared with Stage II patients with normal levels of cICAM-1. Mean survival was also reduced in Stage III patients with abnormally high levels of cICAM-1.

What is claimed is:

1. A method for the detection of organ transplant or tissue graft rejection in a patient, which comprises the steps of:
    a) contacting a sample of one or more bodily fluids in contact with or produced by, the transplanted organ or tissue, with an immobilized first antibody capable of binding to ICAM-1, the immobilized first antibody being insoluble in the sample, to form a first insoluble complex of cICAM-1 and the immobilized first antibody;
    b) contacting the first insoluble complex with a soluble labelled second antibody capable of binding to ICAM-1, to form a final insoluble complex of the labelled second antibody, cICAM-1 and the immobilized first antibody;
    c) separating the final insoluble complex from the sample and any unreacted soluble labelled second antibody;
    d) determining either the amount of label associated with the final insoluble complex or the amount of unreacted label, as a measure of the amount of cICAM-1 in the sample; and
    e) comparing the amount of cICAM-1 in the sample with standards of cICAM-1 normal for the one or more bodily fluids.

2. A method as recited in claim 1 wherein the transplanted organ or tissue is the liver and the bodily fluid is bile.

3. A method as recited in claim 1 wherein the transplanted organ or tissue is the heart and the bodily fluid is plasma.

4. A method for the detection of organ transplant or tissue graft rejection in a patient which comprises measuring the amount of cICAM-1 in a sample of one or more bodily fluids in contact with or produced by the transplanted organ or tissue, and then comparing the amount of cICAM-1 in the sample to standards normal for the one or more bodily fluids.

5. A method for the detection of organ transplant or tissue graft rejection in a patient which comprises the steps of:
    a) contacting a sample of one or more bodily fluids in contact with or produced by the transplanted organ or tissue, with a first antibody capable of binding to ICAM-1 and labelled second antibody capable of binding to ICAM-1;
    b) determining the amount of bound labelled second antibody as a measure of the amount of cICAM-1 in the example; and
    c) comparing the amount of cICAM-1 in the sample with standards of cICAM-1 normal for the one or more bodily fluids assayed.

6. A method as recited in claim 5 wherein the first antibody and the labelled second antibody are monoclonal antibodies.

7. A method as recited in claim 6 wherein the first antibody is immobilized and the labelled second antibody is soluble.

8. A method as recited in claim 7 wherein the immobilized first antibody is immobilized on a solid support.

* * * * *